United States Patent [19]

Denzel et al.

[11] B 3,984,422

[45] Oct. 5, 1976

[54] AMINO DERIVATIVES OF [4,3-c]PYRAZOLOPYRIDINE CARBOXYLIC ACIDS AND ESTERS

[75] Inventors: Theodor Denzel, Regensburg; Hans Hoehn, Tegernheim, both of Germany

[73] Assignee: E. R. Squibb & Sons, Inc., Princeton, N.J.

[22] Filed: Apr. 8, 1974

[21] Appl. No.: 458,617

[44] Published under the second Trial Voluntary Protest Program on February 3, 1976 as document No. B 458,617.

Related U.S. Application Data

[62] Division of Ser. No. 263,566, June 16, 1972, Pat. No. 3,835,144.

[52] U.S. Cl. .................. 260/295.5 B; 260/268 BC; 260/293.6
[51] Int. Cl.$^2$ .................................. C07D 471/06
[58] Field of Search..... 260/293.6, 268 BC, 295.5 B

[56] References Cited
UNITED STATES PATENTS
3,755,340    8/1973    Hoehn et al. .................. 260/293.6

*Primary Examiner*—Henry R. Jiles
*Assistant Examiner*—Robert W. Ramsuer
*Attorney, Agent, or Firm*—Lawrence S. Levinson; Merle J. Smith

[57] ABSTRACT
New amino derivatives of pyrazolo[4,3-c]pyridine-7-carboxylic acids and esters have the general formula

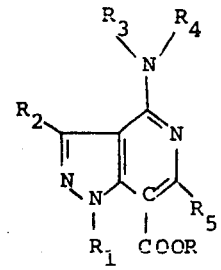

wherein R is hydrogen or lower alkyl; $R_1$ is hydrogen, lower alkyl, phenyl or phenyl—$(C_1-C_2)$— lower alkyl; $R_2$ is hydrogen, lower alkyl, phenyl or phenyl—$(C_1-C_2)$— lower alkyl; the group

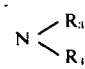

forms one of the heterocyclic groups aziridono, pyrrolidino, piperidino, piperazino, 4-lower alkylpiperazino or 4-(hydroxy-lower alkyl)piperazino; $R_5$ is hydrogen, lower alkyl or phenyl; and physiologically acceptable acid addition salts thereof.

They are useful as ataractic, analgesic and antiinflammatory agents. In addition, the new compounds increase the intracellular concentration of adenosine-3′,5′-cyclic monophosphate.

7 Claims, No Drawings

AMINO DERIVATIVES OF [4,3-c]PYRAZOLOPYRIDINE CARBOXYLIC ACIDS AND ESTERS

This application is a division of application Ser. No. 263,566, filed June 16, 1972, U.S. Pat. No. 3,835,144, issued Sept. 10, 1974.

SUMMARY OF THE INVENTION

This invention relates to new amino derivatives of pyrazolo[4,3-c]pyridine-7-carboxylic acids, their esters and salts of these compounds as well as processes for producing them. These new compounds have the formula (I)

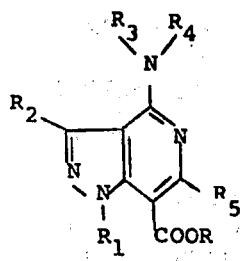

The symbols have the following meanings in formula I and throughout this specification. R is hydrogen or alkyl up to 12 carbon atoms, $R_1$ is hydrogen, lower alkyl, benzoyl, substituted benzoyl (wherein the phenyl ring bears one or two substituents named below), phenyl or phenyl lower alkyl. $R_2$ is hydrogen, lower alkyl, phenyl or phenyl-lower alkyl. The basic nitrogen group

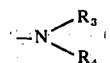

is an acyclic amino moiety wherein $R_3$ and $R_4$ each is hydrogen, lower alkyl, phenyl, substituted phenyl (i.e., the phenyl ring contains one or two simple substituents, preferably lower alkyl, halogen, especially chlorine or trifluoromethyl), phenyl-lower alkyl, di-lower alkylamino-lower alkyl or cyclo-lower alkyl. $R_5$ is hydrogen, lower alkyl or phenyl.

The basic group may also form a heterocycle of 3-, 5- or 6-members in which an additional nitrogen is present, i.e., the aziridinyl, pyrrolidino, piperidino, pyrazolyl, pyrimidyl, pyridazinyl or piperazinyl radicals each of which may also bear as a substituent a hydroxy-lower alkyl group or one or two lower alkyl groups.

The lower alkyl groups in any of the foregoing radicals are straight or branched chain hydrocarbon groups of up to seven carbon atoms like methyl, ethyl, propyl, isopropyl, butyl, t-butyl and the like. The cyclo-lower alkyl groups are the three to six carbon alicyclics, cyclopropyl, cyclobutyl, cyclopentyl or cyclohexyl, especially the last two.

Especially preferred compounds of formula I are those wherein R is hydrogen or lower alkyl, especially ethyl, $R_1$ is hydrogen or ethyl, $R_2$ is methyl, $R_3$ is ethyl, propyl or butyl, $R_4$ is hydrogen and $R_5$ is hydrogen, methyl or ethyl. The examples illustrate other preferred embodiments.

DETAILED DESCRIPTION

The new compounds of formula I may be produced by the following method.

A 5-aminoisoxazole of the formula (II)

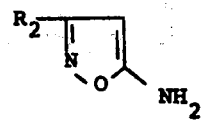

[produced by reacting 3-iminobutyronitrile with hydroxylamine by the procedure described in Ann. Chem. 624, 22 (1959)] is made to react with an alkoxymethylene malonic acid ester of the formula (III)

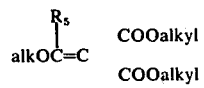

by heating at a temperature of about 120° C.

The resulting compound of the formula (IV)

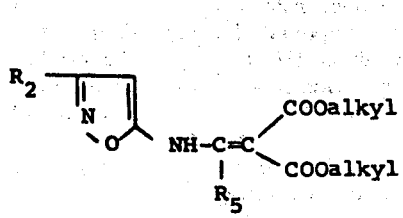

is cyclized in an inert organic solvent, while distilling off the alcohol formed producing a compound of the formula (V)

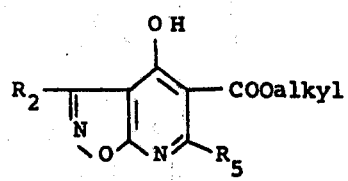

This is then alkylated by treatment with an alkyl halide in an inert organic solvent like dimethylformamide in the presence of an alkali metal carbonate to obtain a compound of the formula (VI)

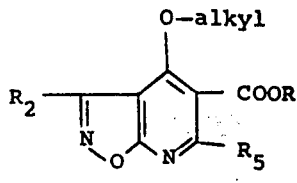

The compound of formula V instead of being alkylated may be refluxed for several hours with a phosphorus halide like phosphorus oxychloride to obtain the intermediate of the formula (VII)

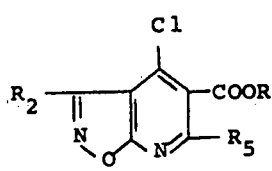

Alternatively, instead of cyclizing the malonic acid ethyl ester compound of formula IV in an inert organic solvent at about 230° to 260° C, this product also undergoes cyclization by means of phosphorus oxychloride producing directly the intermediate of formula VII.

The intermediate of formula VI or of formula VII is then made to react with an amine

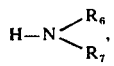

wherein $R_6$ and $R_7$ each is hydrogen, or an aliphatic group like methyl, ethyl and the like. This reaction yields a compound of the formula (VIII)

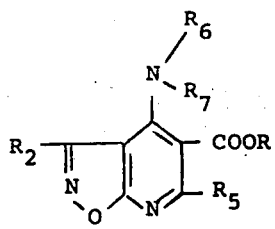

The compound of formula VIII is then hydrogenated with a catalyst like Pd on charcoal in an organic solvent like acetic acid to form a compound of the formula (IX)

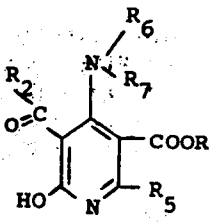

Treatment of the compound of formula IX with hydrazine yields a compound of the formula (X)

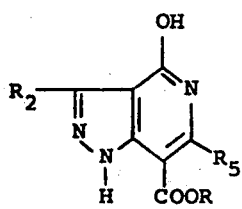

which may be alkylated with an alkyl halide in an inert organic solvent in the presence of an alkali metal carbonate producing a compound of the formula (XI)

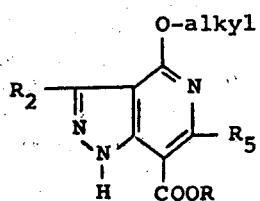

Instead of alkylating, the compound of formula X may be refluxed with an inorganic metal halide, like phosphorus oxychloride, to obtain a compound of the formula (XII)

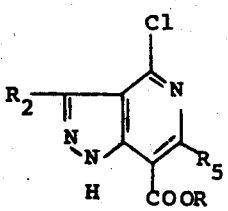

Compounds of formula I are now produced by reacting either compounds of formula XI or XII with an appropriate amine of the formula (XIII)

at elevated temperatures.

Products of formula I with $R_1$ other than hydrogen are produced from compounds of formula I with $R_1$ = H, as described above, by alkylating with a compound of the formula $R_1$-hal, wherein $R_1$ has one of the above defined meanings other than hydrogen, in the presence of a strong base like sodium hydride. Compounds of formula I wherein R is hydrogen are formed from the alkyl esters by conventional hydrolysis, e.g., by treatment with a base such as sodium hydroxide.

The compounds of formula I form salts which are also part of this invention. The salts include acid-addition salts, particularly the non-toxic, physiologically acceptable members. The bases of formula I form salts by reaction with a variety of inorganic or organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating the salt in an appropriate menstruum in which the salt is insoluble, then after separation of the salt, neutralizing with a base such as barium hydroxide or sodium hydroxide, to obtain the free base of formula I. Other salts may then be formed from the free base by reaction with an equivalent of acid.

The new compounds of this invention are central nervous system depressants and may be used as tranquilizers or ataractic agents for the relief of anxiety and tension states, for example, in mice, cats, rats, dogs, and other mammalian species, in the same manner as chlordiazepoxide. For this purpose a compound or mixture of compounds of formula I, or non-toxic, physiologically acceptable acid addition salt thereof, may be administered orally or parenterally in a conventional dosage form such as tablet, capsule, injectable or the like. A single dose, or preferably 2 to 4 divided daily doses, provided on a basis of about 3 to 40 mg. per kilogram per day, preferably about 3 to 15 mg. per kilogram per day, is appropriate. These may be conventionally formulated in an oral or parenteral dosage form by compounding about 10 to 250 mg. per unit of dosage with conventional vehicle, excipient binder, preservative, stabilizer, flavor or the like as called for by accepted pharmaceutical practice.

The new compounds also increase the intracellular concentration of adenosine-3',5'-cyclic monophosphate, and thus by the administration of about 5 to 100 mg/kg/day, preferably about 10 to 50 mg/kg, in single or two to four divided doses in conventional oral or parenteral dosage forms such as those described above may be used to alleviate the symptoms of asthma.

The following examples are illustrative of the invention. All temperatures are on the centigrade scale.

EXAMPLE 1

4-Butylamino-3-methyl-1H-pyrazolo[4,3-c]pyridine-7-carboxylic acid ethyl ester a. [[(3-Methyl-5-isoxazolyl)amino]methylene]malonic acid diethyl ester 112.5 g. of 3-Methyl-5-aminoisoxazole (1.14 mol.) and 248 g. of ethoxymethylenemalonic acid diethyl ester (1.14 mol.) are heated with stirring for 45 minutes at 130°. After this period, ethanol is removed under reduced pressure. The residue solidifies on cooling and is recrystallized from ethanol, m.p. 134°–136°, yield 245 g. (80%).

b. 4-Hydroxy-3-methylisoxazolo[5,4-b]pyridine-5-carboxylic acid ethyl ester 50 g. of [[(3-methyl-5-isoxazolyl)amino]methylene]malonic acid diethyl ester (0.19 mol.) are quickly added to 250 ml. of vigorously refluxing diphenyl ether. After 7 minutes, the reaction mixture is cooled rapidly. The solvent is distilled off in vacuo and the oily residue crystallizes after adding 100 ml. of methanol. Recrystallization from methanol yields 20 g. (48%) of 4-hydroxy-3-methylisoxazolo[5,4-b]pyridine-5-carboxylic acid ethyl ester, m.p. 150°–152°.

c. 4-Ethoxy-3-methylisoxazolo[5,4-b]pyridine-5-carboxylic acid ethyl ester 2.22 g. of 4-Hydroxy-3-methylisoxazolo[5,4-b]pyridine-5-carboxylic acid ethyl ester (0.1 mol.) are dissolved in 150 ml. of ethanol and 28 g. of potassium carbonate (0.2 mol.). 31 g. of ethyl iodide (0.2 mol.) are added. The mixture is heated with stirring for 6 hours. The hot solution is filtered and the solvent evaporated. The oily residue yields on crystallization with methanol 18.2 g. of 4-ethoxy-3-methylisoxazolo-[3,4-b]pyridine-5-carboxylic acid ethyl ester (73%), m.p. 62°.

d. 4-Butylamino-3-methylisoxazolo[5,4-b]pyridine-5-carboxylic acid ethyl ester 25 g. of 4-ethoxy-3-methylisoxazolo[5,4-b]pyridine-5-carboxylic acid ethyl ester (0.113 mol.) are dissolved in 100 ml. of benzene and after adding 8 g. of butylamine (0.23 mol.), the solution is refluxed for 12 hours. The solvent is distilled off and the residual 4-butylamino-3-methylisoxazolo[5,4-b]pyridine-5-carboxylic acid ethyl ester is recrystallized from ligroin, m.p. 60°, yield 23.5 g. (85%).

e. 3-Acetyl-4-butylamino-2-hydroxypyridine-5-carboxylic acid ethyl ester 300 g. of 4-butylamino-3-methylisoxazolo[5,4-b]pyridine-5-carboxylic acid ethyl ester (1.08 mol.) are dissolved in 0.5 liter of acetic acid. 1 g. of palladium on charcoal is added and the mixture is hydrogenated. After absorption of 24 liters of hydrogen, the reaction is stopped, the catalyst is filtered off and the solvent removed in vacuo. The remaining residue is treated for 7 hours at 100° with 0.5 liter of water while stirring. The reaction mixture is cooled and extracted three times with 200 ml. portions of chloroform. The organic layers are collected, dried over sodium sulfate and evaporated to dryness. Recrystallization of the oily residue yields 216 g. of 3-acetyl-4-butylamino-2-hydroxypyridine-5-carboxylic acid ethyl ester (72%), m.p. 134°–136°.

f. 4-Hydroxy-3-methyl-1H-pyrazolo[4,3-c]pyridine-7-carboxylic acid ethyl ester 8.4 g. of 3-acetyl-4-butylamino-2-hydroxypyridine-5-carboxylic acid ethyl ester (0.03 mol.) are dissolved in 20 ml. of acetic acid, 3 ml. of hydrazine-hydrate are added and the mixture is refluxed for 5 hours. After this time, the solvent is removed in vacuo and the crystalline precipitate of 4-hydroxy-3-methyl-1H-pyrazolo[4,3-c]pyridine-7-carboxylic acid ethyl ester is recrystallized from acetic acid, yield 5.1 g. (77%), m.p. 310°.

g. 4-Ethoxy-3-methyl-1H-pyrazolo[4,3-c]pyridine-7-carboxylic acid ethyl ester 2.2g. of 4-hydroxy-3-methyl-1H-pyrazolo[4,3-c]pyridine-7-carboxylic acid ethyl ester (0.01 mol.), 2.8 g. of potassium carbonate (0.02 mol.), and 1.6 g. of ethyl iodide (0.01 mol.) are suspended in 50 ml. of dimethylformamide and heated for 10 hours at 70°. After this time, the mixture is acidified with acetic acid and 30 ml. of water are added. 4-Ethoxy-3-methyl-1H-pyrazolo[4,3-c]pyridine-7-carboxylic acid ethyl ester precipitates, is filtered and recrystallized from methanol, yield 1.9 g. (79%), m.p. 200°.

h. 4-Butylamino-3-methyl-1H-pyrazolo[4,3-c]-pyridine-7-carboxylic acid ethyl ester 2.5 g. of 4-ethoxy-3-methyl-1H-pyrazolo[4,3-c]pyridine-7-carboxylic acid ethyl ester (0.01 g.) are refluxed with 10 ml. of butylamine for 12 hours. After this time, the excess butylamine is distilled off and the residue recrystallized from pettroleum ether, yield 1.9 g. (68%), m.p. 99°–100°. The hydrochloride is formed by adding to the product in ether solution an alcoholic solution of hydrogen chloride.

EXAMPLE 2

4-Diethylamino-3-methyl-1H-pyrazolo[4,3-c]pyridine-7-carboxylic acid ethyl ester a. 4-Chloro-3-methyl-1H-pyrazolo[4,3-c]pyridine-7-carboxylic acid ethyl ester 22.1 g. of 4-hydroxy-3-methyl-1H-pyrazolo[4,3-c]pyridine-7-carboxylic acid ethyl ester (0.1 mol.) and 100 ml. of phosphorus oxychloride are refluxed for 10 hours. After this time, the excess phosphorus oxychloride is removed by distillation. The oily residue is poured into 50 ml. of ice water. On neutralization with aqueous ammonia, 4-chloro-3-methyl-1H-pyrazolo[4,3-c]-pyridine-7-carboxylic acid ethyl ester crystallizes and is filtered. Recrystallization yields 12 g. (50%), m.p. 180°.

b. 4-Diethylamino-3-methyl-1H-pyrazolo[4,3-c]-pyridine-7-carboxylic acid ethyl ester 2.4 g. of 4-chloro-3-methyl-1H-pyrazolo[4,3-c]pyridine-7-carboxylic acid ethyl ester is refluxed with 20 ml. of diethylamine for 24 hours. The excess diethylamine is removed by distillation and the residue treated with 20 ml. of water. 4-Diethylamino-3-methyl-1H-pyrazolo[4,3-c]pyridine-7-carboxylic acid ethyl ester precipitates and is recrystallized from ethyl acetate. Yield 2.1 g. (76%), m.p. 85°–88°. Hydrolysis of this product with aqueous sodium hydroxide yields 4-diethylamino-3-methyl-1H-pyrazolo[4,3-c]pyridine-7-carboxylic acid.

The following additional compounds are produced by the procedure of Example 1:

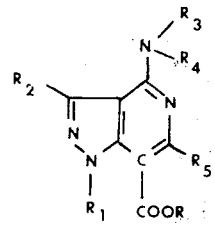

| Example | $R_1$ | $R_2$ | $R_3$ | $R_4$ | $R_5$ | R |
|---|---|---|---|---|---|---|
| 3 | $CH_3-CH_2$ | $CH_3$ | $CH_3-CH_2$ | $CH_3-CH_2$ | $C_2H_5$ | $C_2H_5$ |
| 4 | $CH_3-CH_2$ | H | $-CH_2-CH_2-\underset{CH_3}{N}-CH_2-CH_2-$ | | H | $C_2H_5$ |
| 5 | $CH_3-CH_2$ | H | $-(CH_2)_3N(C_2H_5)_2$ | H | H | $C_2H_5$ |
| 6 | $CH_3-CH_2$ | H | $-CH_2-CH_2-CH_2-CH_2-CH_2-$ | | H | $C_2H_5$ |
| 7 | $CH_3-CH_2$ | H | $CH_3-CH_2$ | $CH_3-CH_2$ | H | $C_2H_5$ |
| 8 | $CH_3-CH_2$ | H | $-(CH_2)_2N(C_2H_5)_2$ | H | H | $C_2H_5$ |
| 9 | $CH_3-CH_2$ | $CH_3$ | H | H | ⌬ | $C_2H_5$ |
| 10 | $CH_3-CH_2$ | H | $-CH_2-\underset{CH_3}{C}=CH-\underset{CH_3}{C}=N-$ | | H | $C_2H_5$ |
| 11 | $CH_3-CH_2$ | $CH_3$ | $-CH_2-CH_2-CH_2-CH_2-$ | | $C_2H_5$ | $C_2H_5$ |
| 12 | $CH_3-CH_2$ | $CH_3$ | $-CH_2-CH_2-CH_2-CH_2-$ | | H | $C_2H_5$ |
| 13 | $CH_3-CH_2$ | H | $-CH_2-CH_2-\underset{CH_2-CH_2-OH}{N}-CH_2-CH_2-$ | | H | $C_2H_5$ |
| 14 | $CH_3-CH_2$ | H | H | H | H | H |
| 15 | $CH_3$ | H | $-(CH_2)_3CH_3$ | H | H | H |
| 16 | $CH_3$ | H | $-(CH_2)_3CH_3$ | H | H | H |
| 17 | $CH_3-CH_2$ | H | $-(CH_2)_3CH_3$ | H | H | H |
| 18 | $CH_3-CH_2$ | $CH_3$ | $-CH=\underset{CH_3}{C}-C=\underset{CH_3}{C}-NH-$ | H | H | $C_2H_5$ |
| 19 | ⌬-$CH_2-$ | $CH_3$ | $-(CH_2)_3CH_3$ | H | H | $C_2H_5$ |
| 20 | H | $CH_3$ | ⌬-$CF_3$ | H | H | $C_2H_5$ |
| 21 | H | H | ⌬-$CF_3$ | H | H | H |
| 22 | H | $CH_3$ | $-CH_2-CH(CH_3)_2$ | H | H | $C_2H_5$ |
| 23 | H | $CH_3$ | $-CH{<}\underset{CH_2-CH_3}{CH_3}$ | H | H | $C_2H_5$ |
| 24 | H | $CH_3$ | $-CH_2-$⌬ | H | H | $C_2H_5$ |

-continued

| Example | R₁ | R₂ | R₃ | R₄ | R₅ | R |
|---|---|---|---|---|---|---|
| 25 | CH₃—CH₂ | CH₃ | —CH₂—CH₂—⬡ | H | H | C₂H₅ |
| 26 | H | CH₃ | —(CH₂)₃CH₃ | H | H | C₂H₅ |
| 27 | CH₃—CH₂ | H | —(CH₂)₃CH₃ | H | H | C₂H₅ |
| 28 | CH₃—CH₂ | H | —CH(CH₃)₂ | H | CH₃ | C₂H₅ |
| 29 | CH₃—CH₂ | H | —(CH₂)₃CH₃ | H | CH₃ | C₂H₅ |
| 30 | CH₃—CH₂ | CH₃ | —(CH₂)₃CH₃ | H | CH₃ | H |
| 31 | CH₃—CH₂ | H | —C(CH₃)₃ | H | ⬡ | C₂H₅ |
| 32 | CH₃—(CH₂)₃ | H | —(CH₂)₃CH₃ | H | H | C₂H₅ |
| 33 | CH₃—CH₂ | H | 2,3-(CH₃)₂-C₆H₃ | H | CH₃ | C₂H₅ |
| 34 | H | H | 2,3-(CH₃)₂-C₆H₃ | H | H | H |
| 35 | CH₃—CH₂ | H | Br-C₆H₄ | H | H | C₂H₅ |
| 36 | CH₃(CH₂)₃ | CH₃ | —(CH₂)₃CH₃ | H | H | C₂H₅ |
| 37 | ⬡ | H | —(CH₂)₃CH₃ | H | H | C₂H₅ |
| 38 | H | CH₃ | —CH₂—CH₂— | H | C₂H₅ |
| 39 | ⬡—CH₂—CH₂— | H | CH₃—(CH₂)₃— | CH₃— | H | CH₃—CH₂— |
| 40 | Cl—C₆H₄—CO— | H | CH₃—CH₂— | H | H | CH₃—CH₂— |
| 41 | Cl—C₆H₄—CO— | CH₃ | CH₃ | CH₃—(CH₂)₃— | H | CH₃—CH₂— |
| 42 | C₆H₅—CO— | H | CH₃—(CH₂)₃— | H | H | CH₃—(CH₂)₆— |
| 43 | CH₃—CH₂—CH₂— | ⬡ | CH₃—(CH₂)₃— | H | CH₃ | CH₃—CH₂ |
| 44 | CH₃—CH₂— | CH₃ | —CH₂—CH₂—N(CH₃)—CH₂—CH₂— | | H | CH₃—CH₂ |
| 45 | H | CH₃ | CH₃—(CH₂)₃— | H | ⬡ | CH₃—CH₂— |
| 46 | CH₃—C₆H₄—CO— | CH₃ | CH₃—(CH₂)₃— | H | H | CH₃—CH₂ |
| 47 | H | CH₃ | CH₃—(CH₂)₃— | H | H | H |
| 48 | H | H | CH₃—(CH₂)₃— | H | C₂H₅ | CH₃—CH₂— |
| 49 | H | H | thienyl | H | H | CH₃—CH₂— |
| 50 | H | H | thienyl | H | H | H |

Other members of the class may similarly be produced by the procedure of Example 1 by suitable substitution of the variables in the starting materials.

What is claimed is:

1. A compound of the formula

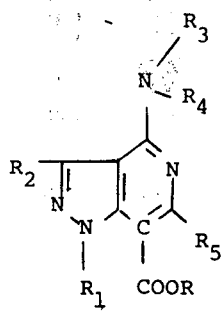

wherein R is hydrogen or lower alkyl; $R_1$ is hydrogen, lower alkyl, phenyl or phenyl—($C_1$-$C_2$)lower alkyl; $R_2$ is hydrogen, lower alkyl, phenyl or phenyl—($C_1$-$C_2$)lower alkyl; the group

forms one of the heterocyclic groups aziridino, pyrrolidino, piperidino, piperazino, 4-lower alkyl-piperazino or 4-(hydroxy-lower alkyl)piperazino; $R_5$ is hydrogen, lower alkyl or phenyl; and physiologically acceptable acid addition salts thereof.

2. A compound as in claim 1 wherein the group

is pyrrolidino.

3. A compound as in claim 1 wherein the group

is aziridino.

4. A compound as in claim 2 wherein R, $R_1$ and $R_2$ each is lower alkyl and $R_5$ is hydrogen.

5. A compound as in claim 2 wherein R and $R_1$ each is ethyl, $R_2$ is methyl and $R_5$ is hydrogen.

6. A compound as in claim 3 wherein R and $R_2$ each is lower alkyl and R and $R_5$ each is hydrogen.

7. A compound as in claim 3 wherein R is ethyl, $R_1$ and $R_5$ each is hydrogen and $R_2$ is methyl.

* * * * *